US009986737B2

(12) United States Patent
Rovison et al.

(10) Patent No.: US 9,986,737 B2
(45) Date of Patent: Jun. 5, 2018

(54) STERILIZATION METHOD

(71) Applicant: PeroxyChem LLC, Philadelphia, PA (US)

(72) Inventors: John M. Rovison, Sanborn, NY (US); Ricky Mittiga, Tonawanda, NY (US); Donald Lapham, Lockport, NY (US); Weidong An, Williamsville, NY (US)

(73) Assignee: PEROXYCHEM LLC, Philadelphia, PA (US)

( * ) Notice: Subject to any disclaimer, the term of this patent is extended or adjusted under 35 U.S.C. 154(b) by 0 days. days.

(21) Appl. No.: 15/060,869

(22) Filed: Mar. 4, 2016

(65) Prior Publication Data

US 2016/0183522 A1   Jun. 30, 2016

Related U.S. Application Data

(63) Continuation of application No. 14/519,351, filed on Oct. 21, 2014, now Pat. No. 9,295,744, which is a continuation of application No. 13/796,439, filed on Mar. 12, 2013, now Pat. No. 8,865,066.

(60) Provisional application No. 61/610,007, filed on Mar. 13, 2012.

(51) Int. Cl.
*A61L 2/00* (2006.01)
*A61L 9/01* (2006.01)
*A01N 37/16* (2006.01)
*A61L 2/20* (2006.01)
*A01N 25/22* (2006.01)

(52) U.S. Cl.
CPC ............ *A01N 37/16* (2013.01); *A01N 25/22* (2013.01); *A61L 2/20* (2013.01); *A61L 2202/24* (2013.01); *Y10S 261/17* (2013.01)

(58) Field of Classification Search
CPC ........ A61L 2/00; A61L 2/0023; A61L 2/0094; A61L 2/06
USPC ............... 422/28; 424/76.8; 134/30, 37, 141
See application file for complete search history.

(56) References Cited

U.S. PATENT DOCUMENTS

| 6,117,457 | A | 9/2000 | Devos et al. |
| 6,475,967 | B1 | 11/2002 | Arvanitidou et al. |
| 6,534,075 | B1 | 3/2003 | Hei et al. |
| 6,544,942 | B1 | 4/2003 | Smith et al. |
| 6,593,283 | B2 | 7/2003 | Hei et al. |
| 6,596,231 | B1* | 7/2003 | Catelli ............... A61L 2/22 422/1 |
| 6,984,360 | B1 | 1/2006 | Feuilloley et al. |
| 6,998,369 | B2 | 2/2006 | Hei et al. |
| 7,569,232 | B2 | 8/2009 | Man et al. |
| 2003/0035754 | A1* | 2/2003 | Sias ............... A61L 2/14 422/29 |
| 2003/0235623 | A1 | 12/2003 | Van Oosterom |
| 2004/0033269 | A1 | 2/2004 | Hei et al. |
| 2005/0084415 | A1* | 4/2005 | McVey ............... A61L 2/186 422/28 |
| 2009/0312292 | A1 | 12/2009 | Rovison et al. |
| 2010/0021558 | A1 | 1/2010 | Dada et al. |
| 2010/0196197 | A1 | 8/2010 | Rovison, Jr. et al. |

FOREIGN PATENT DOCUMENTS

| EP | 0720814 | 7/1996 |
| EP | 1382666 | 1/2004 |
| JP | 2010-526816 | 8/2010 |
| RU | 2195319 | 12/2002 |
| WO | 2008079999 | 7/2008 |
| WO | 2008/140974 | 11/2008 |
| WO | 2010/088594 | 8/2010 |

OTHER PUBLICATIONS

Notice of Grounds of Rejection dated Aug. 30, 2016 issued for corresponding Japanese Application No. 2015-500513.
Notification of Transmittal of The International Search Report and The Written Opinion of the International Searching Authority, or the Declaration; International Application No. PCT/US2013/030487; International Filing Date—Mar. 12, 2013.
First Examination Report dated Dec. 16, 2014 cited in corresponding New Zealand Patent Application No. 700884.

* cited by examiner

*Primary Examiner* — Monzer R Chorbaji
(74) *Attorney, Agent, or Firm* — Duane Morris LLP

(57) ABSTRACT

A method of sterilizing a material, said method comprising the steps of: a) providing a sterilizing composition comprising (i) peracetic acid and (ii) a stabilizer selected from the group consisting of citric acid, isocitric acid, aconitic acid and propane-1,2,3-tricarboxylic acid; b) introducing such sterilizing composition into a hot gaseous stream to produce a peracetic acid vapor; and c) contacting such peracetic acid vapor with the material to be sterilized. The use of such an organic acid stabilizer results in an unexpected reduction in the amount of residue deposited on the heating surface employed to vaporize the sterilizing composition.

17 Claims, No Drawings

STERILIZATION METHOD

FIELD OF THE INVENTION

The present invention is directed to a method of sterilizing a material, said method comprising the steps of: a) providing a sterilizing composition comprising (i) peracetic acid and (ii) a stabilizer selected from the group consisting of citric acid, isocitric acid, aconitic acid and propane-1,2,3-tricarboxylic acid; b) introducing such sterilizing composition into a hot gaseous stream to produce a peracetic acid vapor; and c) contacting such peracetic acid vapor with the material to be sterilized. The use of such an organic acid stabilizer results in an unexpected reduction in the amount of residue deposited on the heating surface employed to vaporize the sterilizing mixture.

BACKGROUND OF THE INVENTION

The necessity of sterilizing surfaces for health and sanitary purposes has long been recognized. Effective sterilization processes are needed for a variety of purposes including aseptic packaging, medical instrument sterilization, biocidal vector environmental remediation, fumigation, vessel sterilization, food stuff treatments, and others.

Among the compounds employed as a sterilizer for such uses is peracetic acid ("PAA"), also called peroxyacetic acid. In order to prolong the shelf-life of PAA compositions, stabilizers are typically added. These stabilizers act as chelators for dissolved metal cations that can disrupt the peroxide bond.

The use of vapor phase peracetic acid to sterilize surfaces is described in US Patent Application 2010/0196197. This publication discloses the use of peracetic acid stabilized with phosphonic acid or acid stabilizers such as Dequest 2010, 1-Hydroxyethylidene-1,1,-diphosphonic acid. While such process is effective to sterilize a variety of different surfaces, it has been found that when such phosphonic acid stabilizers are employed the surface of the heating element used to vaporize the peracetic acid solution tends to become covered with residue over a period of time. This build-up of residue requires that such surface be periodically cleaned, a process which can be time consuming and expensive.

It would therefore be highly desirable to possess a method for using vapor phase peroxyacetic acid as a sterilizing agent which method did not require the relatively frequent cleaning of the heating surfaces of the equipment employed.

While PAA compositions comprising citric acid have been disclosed in the past, such compositions have been employed in liquid aqueous sanitizing applications only. Thus, for example, WO 2008/079999 discloses sterilizing compositions comprised of PAA, citric acid or a salt thereof, and salicylic acid or a salt thereof, which compositions are applied topically to the surfaces to be disinfected employing solution spray systems or the like. Somewhat similarly, U.S. Pat. No. 6,117,457 and European Patent Application 720814 both disclose the use of citric acid in aqueous PAA generation systems; either as a pH regulator in fish ponds or as a means of providing extended PAA generation, respectively.

However, it has now been unexpectedly found that when PAA stabilized with an organic acid such as citric acid is employed in vapor phase sterilization, the buildup of residue on heating surfaces is considerably less than when a phosphonic acid stabilizer is employed. This result is particularly unexpected in view of the showing that aqueous solutions of citric acid (in the absence of PAA) result in the undesirable buildup of residue on heating surfaces.

SUMMARY OF THE INVENTION

The present invention is directed to a method of sterilizing a material, said method comprising the steps of: a) providing a sterilizing composition comprising (i) peracetic acid and (ii) a stabilizer selected from the group consisting of citric acid, isocitric acid, aconitic acid and propane-1,2,3-tricarboxylic acid; b) introducing such sterilizing composition into a hot gaseous stream to produce a peracetic acid vapor; and c) contacting such peracetic acid vapor with the material to be sterilized.

This method permits the effective vapor sterilization of a material without the need for frequently disassembling the apparatus employed in order to remove the buildup of residue which occurs upon the heating surfaces of such apparatus. Accordingly, a wide variety of materials may be rapidly and economically sterilized employing the method of this invention.

DETAILED DESCRIPTION OF THE INVENTION

The present invention is directed to a method of sterilizing a material, said method comprising the steps of: a) providing a sterilizing composition comprising (i) peracetic acid and (ii) a stabilizer selected from the group consisting of citric acid, isocitric acid, aconitic acid and propane-1,2,3-tricarboxylic acid; b) introducing such sterilizing composition into a hot gaseous stream to produce a peracetic acid vapor; and c) contacting such peracetic acid vapor with the material to be sterilized.

As is employed herein, the term vapor means a state in which the peracetic acid is substantially entirely in the gaseous form. This is in contrast to mist or fog, both of which contain a significant proportion of liquid droplets suspended in the air. Unlike the use of a mist or fog, it has been found that the use of peracetic acid in vapor form provides excellent sterilization of materials without the concomitant formation of water droplets on the material surface.

Peracetic acid is typically employed in the form of an aqueous equilibrium mixture of acetic acid, hydrogen peroxide and peracetic acid. The weight ratios of these components may vary greatly, depending upon the particular grade of PAA employed. Among the grades of PAA which may be employed are those having weight ratios of PAA: hydrogen peroxide:acetic acid of from 12-18:21-24:5-20; 15:10:36; 5:23:10; and 35:10:15.

The stabilizer employed in the PAA sterilizing composition is selected from the group consisting of citric acid, isocitric acid, aconitic acid and propane-1,2,3-tricarboxylic acid. Preferably, such stabilizer is citric acid.

Typically, the stabilizer is employed in an amount sufficient to stabilize the PAA for at least three months. Preferably, the stabilizer is present at a concentration sufficient to stabilize the PAA for a period of at least six months.

In general, such stabilizer will typically be present in an amount of between about 0.75% and about 1.5%; preferably of between about 0.9% and 1.25%; and more preferably of between about 1.0% and about 1.2%; all such percentages being by weight, based upon the total weight of the PAA composition.

The composition employed in the process of this invention may further comprise sequestrants such as dipicolinic acid, as well as other ingredients such as mineral acid catalysts (sulfuric, nitric, or phosphoric acids); surfactants such as anionic laurylates, sorbitans and their respective esters, i.e. polyethylene sorbitan monolaurylates; and short chain fatty esters (C6-C12) forming mixed peracids in solution.

In addition, the compositions employed in the process of this invention may further comprise one or more additional oxidants selected from the group consisting of chloroperbenzoic acid, perheptanoic acid, peroctanoic acid, perdecanoic acid, performic acid, percitric acid, perglycolic acid, perlactic acid and perbenzoic acid.

In the practice of the process of this invention, the peracetic acid sterilizing composition is preferably diluted, prior to its introduction into the heated gas stream, by the addition of high quality water (deionized water with ≥2 MOhm resistivity or ≤0.5 μSiemens conductivity), to a concentration of less than about 10,000 parts per million (ppm) of PAA, preferably to a concentration of less than about 4,000 ppm PAA.

The heated gas stream is typically sterile air, although other gases such as nitrogen, $CO_2$, or inert noble gas carriers may also be employed. Such gas stream is typically heated to a temperature of at least about 300° C., preferably to a minimal temperature of about 250° C. and can be in excess of 350° C. providing it can be cooled sufficiently for application. It then is typically cooled to between about 80° C. and about 120° C. prior to the introduction of the peracetic acid solution. The heated gas stream at the point of peracetic acid introduction should have a temperature of at least 5° C. higher than the dew point of peracetic acid (ca. 46.5°-49.9° C.); i.e., of at least about 55° C., in order to ensure that the peracetic acid is converted into a vapor rather than a fog or mist.

The peracetic acid may be introduced into the heated air stream by any means well known to one of skill in the art. One preferred method is by direct injection of a solution.

The peracetic acid vapor is then contacted with the material to be sterilized for a period sufficient to kill the contaminants of concern. This time period will vary according to variables such as the concentration of the peracetic acid vapor employed; the nature of the surface of the material to be sterilized; the particular contaminants to be sterilized; the concentration of the contaminants to be sterilized; and the like. Typically, such contact will maintained for a period of between about 15 and about 40 minutes.

A wide variety of materials may be sterilized employing the method of this invention, including hard surfaces of metals, plastics, polymers, and elastomers.

The present method may be used to sterilize materials contaminated with those bacteria typically controlled by peracetic acid in the liquid form. These include bacteria and spores of the genus *Bacillus* using *B. thuringiensis* and *B. atrophaeus* as surrogates for more pathogenic species (forms) such as *C. botulinum* as well as more typical genera of bacteria, fungi, and viruses and protozoans often controlled by PAA such as (but not limited to): *Staphlococcus, Enterococcus, Salmonella, Campylobacter, Pseudomonas, Candida, Rhizopus, Mucor, Influenza, Bacilli*, etc.

The following Examples are presented to offer further illustration of the present invention, but are not intended to limit the scope of the invention in any manner whatsoever.

Example 1

In order to demonstrate the stabilizing effect of citric acid on PAA compositions, varying amounts of citric acid were added to concentrated PAA compositions, which compositions were stored at room temperature. Periodically, at the times indicated in Tables 1-4 below, samples of such compositions were analyzed for their peracetic acid (PAA); hydrogen peroxide ($H_2O_2$); and acetic acid (AA) contents (in percent by weight); and their Active Oxygen Recovery percentage (AO Rec) was calculated. The data presented in such Tables indicates that citric acid alone can stabilize PAA compositions for extended periods of more than 3 or 6 months.

TABLE 1

0.91% Citric Acid

| Days After Addition | PAA % | $H_2O_2$ % | AA % | AO Rec % |
|---|---|---|---|---|
| — | 0.8438 | 15.0778 | 49.4288 | 88.94 |
| 1 | 2.8207 | 14.4139 | 47.1477 | 90.21 |
| 2 | 4.8579 | 13.7938 | 45.1340 | 91.89 |
| 3 | 6.8554 | 13.1946 | 43.4419 | 93.58 |
| 4 | 8.1230 | 12.7316 | 42.2202 | 94.18 |
| 8 | 12.1365 | 11.4882 | 38.1054 | 97.35 |
| 9 | 11.8892 | 11.2862 | 37.8752 | 95.55 |
| 10 | 12.8904 | 11.1100 | 37.6596 | 97.12 |
| 11 | 13.3851 | 11.0106 | 36.8579 | 97.82 |
| 14 | 15.3285 | 10.6744 | 35.9054 | 100.89 |
| 15 | 14.4656 | 10.6141 | 35.8921 | 98.32 |
| 16 | 14.7712 | 10.5483 | 36.6383 | 98.72 |
| 17 | 15.4082 | 10.5003 | 36.1812 | 100.09 |
| 18 | 15.0226 | 10.4909 | 36.6624 | 99.04 |
| 21 | 15.3530 | 10.3126 | 35.4124 | 98.87 |
| 28 | 16.1285 | 10.1703 | 34.9291 | 100.04 |
| 36 | 16.0191 | 10.0980 | 34.7712 | 99.35 |
| 43 | 16.6856 | 10.0932 | 34.0215 | 101.03 |
| 77 | 15.7208 | 9.8166 | 35.5012 | 96.96 |
| 95 | 15.8097 | 9.8772 | 35.7577 | 97.54 |
| 133 | 15.4084 | 9.7041 | 35.5974 | 95.51 |
| 162 | 14.2637 | 9.6438 | 36.2839 | 92.21 |
| 197 | 14.8616 | 9.5118 | 35.3907 | 92.99 |
| 228 | 14.5168 | 9.4222 | 35.9890 | 91.59 |
| 260 | 13.9939 | 9.2273 | 36.6908 | 89.12 |
| 285 | 13.8226 | 9.1102 | 36.1968 | 88.01 |
| 314 | 14.2674 | 9.0070 | 36.6037 | 88.56 |
| 344 | 13.3877 | 8.9848 | 36.4208 | 86.17 |
| 378 | 13.5115 | 8.8263 | 36.9739 | 85.57 |
| 403 | 13.0327 | 8.6849 | 37.7293 | 83.53 |

TABLE 2

1.00% Citric Acid

| Days After Addition | PAA % | $H_2O_2$ % | AA % | AO Rec % |
|---|---|---|---|---|
| — | 0.8688 | 17.1802 | 47.8195 | 101.08 |
| 1 | 2.8990 | 15.7369 | 45.8501 | 98.00 |
| 2 | 5.1241 | 14.8095 | 43.8144 | 98.39 |
| 3 | 7.1400 | 13.9885 | 42.6610 | 98.86 |
| 4 | 8.4730 | 13.3357 | 41.1202 | 98.53 |
| 8 | 12.0610 | 11.7606 | 37.6254 | 98.70 |
| 9 | 12.8241 | 11.5194 | 37.3773 | 99.28 |
| 10 | 13.1537 | 11.3034 | 37.6218 | 98.88 |
| 11 | 13.3192 | 11.1213 | 37.4239 | 98.26 |
| 14 | 14.8345 | 10.7323 | 36.7059 | 99.92 |
| 15 | 14.8165 | 10.6578 | 36.3016 | 99.45 |
| 16 | 14.8555 | 10.5471 | 35.7440 | 98.91 |
| 17 | 14.9233 | 10.5083 | 36.4307 | 98.86 |
| 18 | 15.1771 | 10.4201 | 35.2700 | 99.01 |
| 21 | 15.5752 | 10.2907 | 35.7839 | 99.29 |
| 28 | 16.0195 | 10.1210 | 34.7292 | 99.45 |
| 36 | 15.4584 | 10.0619 | 35.0277 | 97.67 |
| 43 | 15.9848 | 10.0408 | 34.6613 | 98.90 |
| 77 | 15.6363 | 9.8988 | 35.8995 | 97.19 |
| 95 | 15.4839 | 9.8409 | 34.7765 | 96.46 |
| 133 | 15.0663 | 9.6691 | 36.3532 | 94.40 |

TABLE 2-continued

1.00% Citric Acid

| Days After Addition | PAA % | H$_2$O$_2$ % | AA % | AO Rec % |
|---|---|---|---|---|
| 162 | 14.8545 | 9.6176 | 36.6276 | 93.56 |
| 197 | 14.8315 | 9.477 | 35.6838 | 92.69 |
| 228 | 14.4704 | 9.3548 | 36.0888 | 91.06 |
| 260 | 15.0582 | 9.2067 | 35.5108 | 91.72 |
| 285 | 14.3021 | 9.0621 | 36.2798 | 88.94 |
| 314 | 14.197 | 8.956 | 37.3694 | 88.06 |
| 344 | 13.9533 | 8.8917 | 36.8442 | 87.06 |
| 378 | 13.1943 | 8.7715 | 37.5735 | 84.42 |
| 403 | 12.9297 | 8.6296 | 37.1723 | 92.82 |

TABLE 3

1.15%, Citric Acid

| Days After Addition | PAA % | H$_2$O$_2$ % | AA % | AO Rec % |
|---|---|---|---|---|
| — | 0.9493 | 14.9203 | 49.7722 | 88.31 |
| 1 | 2.7103 | 14.0927 | 47.8537 | 88.08 |
| 2 | 4.8674 | 13.5088 | 45.8163 | 90.27 |
| 3 | 6.7840 | 12.8510 | 44.2981 | 91.42 |
| 4 | 8.0746 | 12.4248 | 42.6000 | 92.29 |
| 8 | 11.8005 | 11.2592 | 38.8622 | 95.17 |
| 9 | 12.7506 | 11.1215 | 37.9775 | 96.82 |
| 10 | 13.0775 | 10.9839 | 37.7389 | 96.87 |
| 11 | 13.7122 | 10.8617 | 38.0374 | 97.80 |
| 14 | 14.4521 | 10.6744 | 36.8023 | 98.63 |
| 15 | 14.7832 | 10.5997 | 36.0188 | 99.05 |
| 16 | 14.9035 | 10.5517 | 35.5883 | 99.09 |
| 17 | 14.9890 | 10.5392 | 35.5743 | 99.23 |
| 18 | 15.1184 | 10.4180 | 35.4307 | 98.87 |
| 21 | 15.7941 | 10.3115 | 35.4520 | 100.00 |
| 28 | 16.1877 | 10.1272 | 34.7089 | 99.95 |
| 36 | 15.0727 | 10.0837 | 34.9070 | 96.83 |
| 43 | 15.8094 | 10.0461 | 35.0496 | 98.51 |
| 77 | 15.5986 | 9.8953 | 35.6593 | 97.10 |
| 95 | 15.5719 | 9.8333 | 35.9455 | 96.67 |
| 133 | 16.0577 | 9.6417 | 34.8538 | 96.82 |
| 162 | 15.1268 | 9.5816 | 36.0882 | 94.08 |
| 197 | 15.7167 | 9.5183 | 34.8321 | 95.23 |
| 228 | 13.9662 | 9.3003 | 36.2149 | 89.47 |
| 260 | 13.4297 | 9.1271 | 36.3155 | 87.09 |
| 285 | 14.3050 | 9.0125 | 36.4291 | 88.69 |
| 314 | 13.5222 | 8.9160 | 36.6740 | 86.12 |
| 344 | 13.8437 | 8.8414 | 37.2805 | 86.51 |
| 378 | 13.0769 | 8.7360 | 47.0423 | 83.93 |
| 403 | 12.9157 | 8.5879 | 37.2918 | 82.67 |

TABLE 4

1.24% Citric Acid

| Days After Addition | PAA % | H$_2$O$_2$ % | AA % | AO Rec % |
|---|---|---|---|---|
| — | 0.7259 | 12.9350 | 51.4255 | 76.31 |
| 1 | 2.6857 | 13.1213 | 48.8097 | 82.42 |
| 2 | 4.7080 | 12.8994 | 46.6388 | 86.35 |
| 3 | 6.6668 | 12.4803 | 45.0566 | 88.98 |
| 4 | 8.1618 | 12.0665 | 43.2028 | 90.45 |
| 8 | 12.3648 | 11.1363 | 39.9843 | 95.91 |
| 9 | 12.5204 | 10.9715 | 38.9763 | 95.37 |
| 10 | 13.1867 | 10.8514 | 38.4447 | 96.39 |
| 11 | 13.8380 | 10.7723 | 37.6754 | 97.61 |
| 14 | 14.3456 | 10.5460 | 36.8458 | 97.62 |
| 15 | 14.6369 | 10.5380 | 36.0910 | 98.32 |
| 16 | 14.7992 | 10.4648 | 35.8426 | 98.43 |
| 17 | 14.9864 | 10.4538 | 35.7862 | 98.74 |
| 18 | 15.3825 | 10.4189 | 36.6292 | 99.55 |
| 21 | 15.3706 | 10.2649 | 35.4215 | 98.64 |

TABLE 4-continued

1.24% Citric Acid

| Days After Addition | PAA % | H$_2$O$_2$ % | AA % | AO Rec % |
|---|---|---|---|---|
| 28 | 15.8088 | 10.1306 | 35.0317 | 98.99 |
| 36 | 15.8843 | 10.0424 | 35.1196 | 98.68 |
| 43 | 15.9236 | 10.0629 | 35.2217 | 98.90 |
| 77 | 15.6937 | 9.8773 | 35.6800 | 97.24 |
| 95 | 15.7823 | 9.7861 | 36.1936 | 96.94 |
| 133 | 15.1511 | 9.6406 | 35.6101 | 94.48 |
| 162 | 15.0181 | 9.5280 | 36.4564 | 94.39 |
| 197 | 15.5437 | 9.3555 | 35.0428 | 93.85 |
| 228 | 14.1509 | 9.2284 | 36.2681 | 89.53 |
| 260 | 14.9844 | 9.0772 | 35.7010 | 90.81 |
| 285 | 14.3708 | 8.9362 | 36.5596 | 88.42 |
| 314 | 14.1109 | 8.7402 | 36.4426 | 86.62 |
| 344 | 13.9393 | 8.7677 | 36.9396 | 86.34 |
| 378 | 13.4533 | 8.6343 | 37.2074 | 84.32 |
| 403 | 13.3214 | 8.5447 | 38.2168 | 83.46 |

Example 2

In order to determine the amount of residue buildup produced by vaporization, various solutions were prepared by blending the following ingredients:

Samples A1, A2 and A3: 250 ppm citric acid in deionized water

Sample B 1: 4000 ppm PAA+about 24 ppm Dequest 2010

Samples C1 and C2: 4000 ppm PAA+250 ppm citric acid

The PAA employed had a PAA:hydrogen peroxide:acetic acid weight ratio of about 15:10:36.

An initial portion of the sample to be tested was placed into a 50 mL burette suspended over a 100 mL beaker placed on a Corning Stirrer/Hotplate. The hotplate was heated to 180° C. and the stopcock on the burette opened such that the solution was added drop wise for vaporization. The burette was refilled before it ran out of solution. The hotplate was shut off and the beaker allowed to return to room temperature. Once it had cooled to room temperature, the beaker was reweighed to determine the amount of residue present. The results observed and the calculated amount of residue (mg/mL) are summarized in Table 5 below.

TABLE 5

| Sample | Residue (mg) | Volume of Solution (mL) | Mg/mL of Residue |
|---|---|---|---|
| A1 | 20 | 92.5 | 0.22 |
| A2 | 31 | 109.9 | 0.28 |
| A3 | 27 | 117 | 0.23 |
| B1 | 131 | 94.3 | 1.39 |
| C1 | 0 | 121.6 | 0.00 |
| C2 | 3 | 92 | 0.03 |

The above results show that the method of the present invention (exemplified in Samples C1 and C2) produces considerably less residue of the heating surface than does a PAA composition of equal concentration which is stabilized using a phosphonate stabilizer. This result is completely unexpected in view of the showing that the vaporization of citric acid in deionized water results in the formation of a much more residue than does the vaporization of a composition comprising an equal amount of citric acid in a PAA solution.

What is claimed is:

1. A method of sterilizing a material, wherein the material is selected from the group consisting of metals, plastics, polymers and elastomers, the method comprising the steps of:
   a) providing a sterilizing composition comprising (i) peracetic acid and (ii) a stabilizer selected from the group consisting of citric acid, isocitric acid, aconitic acid and propane-1,2,3-tricarboxylic acid;
   b) introducing the sterilizing composition into a hot gaseous stream, wherein the temperature of the hot gaseous stream at the point of peracetic acid introduction is at least 5° C. higher than the dew point of peracetic acid, to produce a peracetic acid vapor; and
   c) contacting the peracetic acid vapor with the material to be sterilized.

2. The method of claim 1, wherein the peracetic acid is present in a concentration of from about 15 to about 17 weight percent of the sterilizing composition; and the stabilizer is present in an amount between about 0.75 and about 1.5 weight percent of the sterilizing composition.

3. The method of claim 2, wherein the stabilizer is present in an amount between about 0.9 and about 1.25 weight percent of the sterilizing composition.

4. The method of claim 3, wherein the stabilizer is present in an amount between about 1.0 and about 1.2 weight percent of the sterilizing composition.

5. The method of claim 1, wherein the peracetic acid is an aqueous equilibrium composition having a peracetic acid:hydrogen peroxide:acetic acid weight ratio selected from the group consisting of 12-18: 21-24:5-20; 15:10:36; 5:23:10; 21-23:6-10:33-36; and 35:10:15.

6. The method of claim 1, wherein the peracetic acid is diluted to a concentration of less than 10,000 ppm prior to being introduced into the hot gaseous stream.

7. The method of claim 6, wherein the peracetic acid is diluted to a concentration of less than 4,000 ppm prior to being introduced into the hot gaseous stream.

8. The method of claim 1, wherein the stabilizer comprises citric acid.

9. The method of claim 8, wherein the citric acid is diluted to about 250 ppm prior to being introduced into the hot gaseous stream.

10. The method of claim 1, wherein the hot gaseous stream comprises sterile air, nitrogen, carbon dioxide or an inert noble gas.

11. The method of claim 1, wherein the hot gaseous stream is heated to a temperature above about 250° C. prior to the introduction of the peracetic acid.

12. The method of claim 1, wherein the hot gaseous stream is heated to a temperature above about 250° C. and is then cooled to a temperature of between about 80° C. and about 120° C. prior to the introduction of the peracetic acid.

13. The method of claim 1, wherein the material to be sterilized is contaminated with bacteria or spores of *Clostridium botulinum, Bacillis thuringensis*, or *Bacillus atrophaeus*.

14. The method of claim 1, wherein the material to be sterilized is contaminated with one or more of *Staphylococcus, Enterococcus, Salmonella, Campylobacter, Pseudomonas, Candida, Rhizopus, Mucor*, or *Influenza*.

15. The method of claim 1, wherein the sterilizing composition further comprises one or more oxidants selected from the group consisting of chloroperbenzoic acid, perheptanoic acid, peroctanoic acid, perdecanoic acid, performic acid, percitric acid, perglycolic acid, perlactic acid and perbenzoic acid.

16. The method of claim 1, wherein the sterilizing composition further comprises a sequestrant, a mineral acid catalyst, a surfactant, or a short chain fatty ester.

17. The method of claim 1, wherein the contacting step is maintained for about 15 minutes to about 40 minutes.

* * * * *